United States Patent [19]

Kensho et al.

[11] Patent Number: 5,137,921

[45] Date of Patent: Aug. 11, 1992

[54] INHIBITORY AGENT OF AN INCREASE IN BLOOD SUGAR LEVEL

[75] Inventors: Ituo Kensho, Houya; Fumio Yamashita, Sagamihara; Toshikazu Nagai, Machida; Tadashi Fujimoto, Yamato; Yoshihisa Nakano, Sakai; Hideki Tukimura, Yokohama, all of Japan

[73] Assignee: Dai-Nippon Sugar Mfg. Co., Ltd., Tokyo, Japan

[21] Appl. No.: 736,420

[22] Filed: Jul. 26, 1991

[30] Foreign Application Priority Data

Sep. 3, 1990 [JP] Japan ................................ 2-230500
Jul. 17, 1991 [JP] Japan ................................ 3-176906

[51] Int. Cl.$^5$ .................... A61K 31/045; C07C 35/08; C07C 35/18; C07D 303/14
[52] U.S. Cl. .................... 514/729; 549/546; 560/231; 568/667; 568/823; 568/837
[58] Field of Search .................... 568/823; 514/729

[56] References Cited

U.S. PATENT DOCUMENTS 4,761,286  8/1988  Hiji ............................. 424/195.1
4,988,682  1/1991  Kozikowski ...................... 514/729

OTHER PUBLICATIONS

Sutbeyaz et al., J. Chem. Soc., Chem. Commun., 1330-1331 (1988).
Cambie, Synthetic Communications, 19, 537,546 (1989).
Legler et al., Carbohydrate Research, 28, 45-52 (1973).
Braun, Biochimica et Biophysica Acta, 485, 141-146 (1977).
Stephens et al., Biochimica et Biophysica Acta, 672, 29-32 (1981).
Shou-jun et al., Biochimica et Biophysica Acta, 828, 236-240 (1985).
Legler et al., Archives of Biochemistry and Biophysics, 260, 437-442 (1988).
Fujimoto et al., Biochemistry, 62, 0199 (1990).
Legler et al., Hoppe-Seyler's Z. Physiol. Chem., 354, 243-254 (1973).

*Primary Examiner*—J. E. Evans
*Attorney, Agent, or Firm*—Finnegan, Henderson, Farabow, Garrett and Dunner

[57] ABSTRACT

There is provided an inhibitory agent of an increase in blood sugar level, comprising conduritol A of the formula(I):

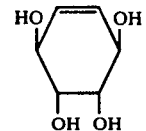

(I)

or a derivative thereof, as an active component.

1 Claim, No Drawings

INHIBITORY AGENT OF AN INCREASE IN BLOOD SUGAR LEVEL

INDUSTRIAL APPLICABILITY

The present invention relates to an inhibitory agent of an increase in blood sugar level, which comprises a particular monosaccharide or a derivative thereof as an active component.

PRIOR ART

Conduritol has 6 isomers, namely conduritol A, B, C, D, E and F. Among them, conduritol A is known to occur in condurango, the bark of Condurango vine, and is a monosaccharide represented by the formula (I):

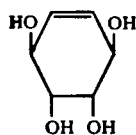

Condurango vine is a vine *Marsdenia condurango* Reichbach fil belonging to the family Asclepiadaceae the habitat of which is North Western region of South America. The powder and fluidextract of the bark of Condurango vine are incorporated into the 11th Japanese Pharmacopeia as D-332 and D-334, respectively, as fragrant stomachic. However, an inhibitory action of conduritol A on an increase of blood sugar level has not heretofore been known. Gymnemic acid extracted from *Gymnema sylvestre* which is also a vine belonging to the family Asclepiadaceae and originally grows in India, is known to have an inhibitory action on the absorption of sugar in intestinal tract, leading to the inhibition of an increase in blood sugar level (Japanese Patent Laid-Open-to-Public Publication No. 5023/1986). However, the inhibitory action of conduritol A which can be extracted from *Gymnema sylvestre* on an increase of the blood sugar level has not been known, also.

Though conduritol A can be obtained by extracting and purifying the plants *Gymnema sylvestre, Marsdenia condurango*, etc., it can also be obtained by chemical synthesis.

Conduritol A is one of cyclits (i.e., cyclic polyhydric alcohol) and structurally analogous to naturally occurring inositol. Therefore, there is a possibility of obtaining conduritol A or a derivative thereof from inositol. Presently, however, production of conduritol A or a derivative thereof from inositol has been known only partly (see, hereinafter). In addition, an inhibitory action on an increace in blood sugar level of these compounds has never been known.

SUMMARY OF THE INVENTION

An object of the present invention is to provide a new inhibitory agent of an increase in blood sugar level, which comprises conduritol A or a derivative thereof as an active component.

It has surprisingly been found that conduritol A and derivatives thereof have effective inhibitory action on the absorption of sugar in intestinal tract, according to sugar absorption test using reversed gut, and that they effectively inhibit an increase in the blood sugar level after oral administration of sugar in rat. Conduritol A and derivatives thereof can inhibit rapid increase in blood sugar level after ingestion of sugar at meals, thus reducing the load of secreting insulin. Therefore, they are useful as a therapeutic agent for treating diabetes.

An object of the invention is to provide an inhibitory agent of an increase in blood sugar level, comprising conduritol A as an active component.

Another object of the invention is to provide an inhibitory agent which comprises conduritol A derivative as an active component.

Further object of the invention is to provide an inhibitory agent in which said conduritol A derivative is represented by the formula (II):

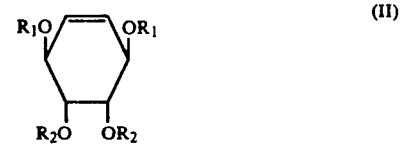

wherein $R_1$ and $R_2$ are H, Ac or lower alkyl, provided that $R_1$ and $R_2$ do not represent H simultaneously. Exemplary compounds are tetraacetyl-conduritol A ($R_1=R_2=Ac$), tetramethoxy-conduritol A ($R_1=R_2=Me$), 3, 6-dimethoxy-conduritol A ($R_1=Me$, $R_2=H$), and 3, 6-diacetyl-conduritol A ($R_1=Ac$, $R_2=H$).

Still further object of the invention is to provide an inhibitory agent in which said conduritol A derivative is tetraacetylconduritol A of the formula(III)

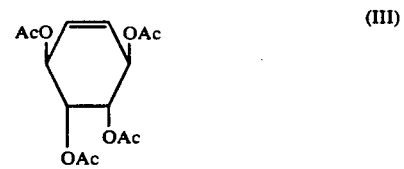

Still further object of the invention is to provide an inhibitory agent in which said conduritol A derivative is dihydroconduritol A of the formula(IV):

Still further object of the invention is to provide an inhibitory agent in which said conduritol A derivative is conduritol A epoxide of the formula(V):

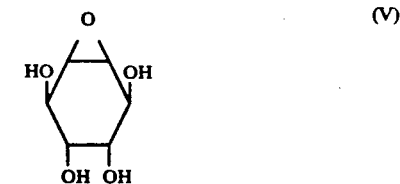

Conduritol A used in the present invention may be obtained from dried leaves of *Gymnema sylvestre* or from dried bark of *Marsdenia condurango* by means of extraction, or may be chemicaly synthesized according to known methods (R. C. Cambie et al., Synthetic Communications, 19: 537(1989); Y. Sütbeyaz et al., J. Chem. Soc., Chem. Commun., 1330(1988)).

The conduritol A derivatives as described above can be prepared from conduritol A according to the methods as set forth below in Examples 3-5. They have been found to have the same or even higher activity than that of conduritol A.

The physicochemical properties of conduritol A are as follows:

(1) $^1$H-NMR: $\delta=3.85$(d, J=4.5, 2H, H2, 3), 4.22(d, J=4.5, 2H, H1, 4), 5.80(s, 2H, H5, 6) (R. C. Cambie et al., Synthetic Communications, 19: 537(1989), (2) FT-IR: 3038(C—H), 1635(C=C), 1317, 1290 cm$^{-1}$, (3) Melting Point: 147° C.,

| (4) Elementary Analysis calculated for $C_6H_{10}O_4$: | | | |
|---|---|---|---|
| | C % | H % | O % |
| Calc'd | 49.32 | 6.85 | 43.82 |
| Found | 49.13 | 6.87 | 44.00, |

(5) Optical Rotation: $[\alpha]_D^{20}$ 0.00° (in H$_2$O), (6) Shape of Crystals: Needles (from ethanol/n-hexane), (7) GC-MS (TMSization): m/z 434, 332, 230, 204.

The physicochemical properties of conduritol A derivatives are as follows:

Tetraacetyl Conduritol A:

(1) Chemical formula: $C_{14}H_{18}O_8$, Molecular Weight: 314, Boiling Point: 152° C.(0.2 mg Hg) (amorphous) (Gerda Dangschat and Hermann O. L. Fischer, Carbohydrate Research 164: 343-355, 1987);

| (2) Elementary Analysis calculated for $C_{14}H_{18}O_8$: | | | |
|---|---|---|---|
| | C % | H % | O % |
| Calc'd | 53.51 | 5.73 | 40.76 |
| Found | 53.29 | 5.81 | 40.90; |

(3) $^1$H-NMR: $\delta=2.10$(d, J=5.8, 12H), 5.34(d, J=5.2, 2H, H2, 3), 5.42(d, J=4.6, 2H, H1,4), 5.88(s, 2H, H5, 6);

(4) FT-IR: 2948(—CH=CH—), 1747(—CO—), 1372(C—CH$_3$) cm$^{-1}$,

Dihydroconduritol A:

(1) Chemical formula: $C_6H_{12}O_4$, Molecular Weight: 148, Melting Point: 207° C. (Howard A. J. Carless and Ozer Z. Oak, Tetrahedron Letters 30: 13, 1719-1720, 1989);

| (2) Elementary Analysis calculated for $C_6H_{12}O_4$: | | | |
|---|---|---|---|
| | C % | H % | O % |
| Calc'd | 48.65 | 8.11 | 43.24 |
| Found | 48.51 | 8.13 | 43.36; |

(3) $^1$H-NMR: $\delta=1.52$(m, 4H), 4.35(d, 4H);

(4) FT-IR: 2891(—CH$_2$—, dimer), 1463(—CH$_2$—, bending) cm$^{-1}$,

Conduritol A Epoxide:

(1) Chemical formula: $C_6H_{10}O_5$, Molecular Weight: 162, Melting Point: 110° C. (Nakajima Minoru and Kurihara Norio, Chem. Ber., 94: 515-522, 1961);

| (2) Elementary Analysis calculated for $C_6H_{10}O_5$: | | | |
|---|---|---|---|
| | C % | H % | O % |
| Calc'd | 44.45 | 6.17 | 49.38 |
| Found | 44.40 | 6.22 | 49.38; |

(3) $^1$H-NMR: $\delta=3.55$(d, J=2.4, 2H, H5, 6), 3.70(d, J=4.5, 2H, H2, 3), 4.10(d, J=6.7, 2H, H1, 4);

(4) FT-IR: 3053(C—H, epoxide), 1274

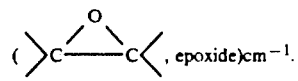

, epoxide)cm$^{-1}$.

The above mentioned compounds are shown for exemplary purpose only, and other derivatives including hydrogenated, methylated or partially acetylated derivatives are also expected to exhibit similar pharmacological activities and therefore contemplated to be used in the agent of the present invention.

The inhibitory agent of this invention may be prepared by formulating conduritol A or a derivative thereof as an active component using conventional pharmaceutical additives such as solid or liquid diluents, excipients, stabilizers, etc., to form various dosage forms suitable for oral or enteral administration such as granules, particles, powders, tablets, capsules, pills, liquids, and the like. The amount of the active component may range from 1 to 90% by weight of the formulation. Preferably, the amount of the active component is in the range of 5-80% by weight for solid preparations and 1-30% by weight for liquid preparations. The active component of the present invention may also be administered without any additives.

Any pharmaceutically acceptable organic or inorganic, solid or liquid excipients or diluents suitable for oral or enteral administration may be used for the preparation of the inhibitory agent of the present invention. Suitable examples are water, gelatine, lactose, starches, magnesium stearate, talc, oils and fats of animal and vegetable origins, benzyl alcohol, gums, polyalkylene glycol, petroleum resin, coconut oil, lanolin, etc. Other pharmaceutically acceptable additives such as stabilizers, wetting agents, emulsifiers, tonic adjusting agents, pH-adjusting agents and the like may also be added.

The agent of the present invention may be administered together with other therapeutic agents used for the treatment of diabetes.

Suitable daily dose for adults of conduritol A or a derivative for oral administration is in the range of 10-3000 mg, but above or below said limit is possible depending on the age and conditions of the patient to be treated. Said daily dose may either be applied once a day, or preferably subdivided into 2 or 3 portions and administered with an appropriate intervals.

EXAMPLE

The invention is further illustrated, but not limited, by the following Examples.

EXAMPLE 1

The dried leaves of *Gymnema sylvestre* were extracted with 30% ethanol, the extract was distilled to remove ethanol and the residual aqueous solution was adjusted to pH 1.5 with hydrochloric acid. The precipitate formed was removed by centrifugation. The supernatant was neutralized with the addition of sodium hydroxide, and deionized by passing through an ion exchange column packed with both anionic and cationic resins. The deionized solution was passed through an active carbon column and eluted with water. The eluate was concentrated under reduced pressure to dryness. The residue was dissolved in n-propanol, passed through an active alumina column, eluted with n-propanol, and the eluate was concentrated under reduced pressure. 10 times the volume of the residue, of absolute alcohol was added to the residue and the precipitate formed was dried in vacuo, to afford white powder of pure conduritol A.

EXAMPLE 2

The dried bark of Condurango vine was pulverized and soaked in n-hexane, then filtered and the residue was dried to remove n-hexane completely. The residue was worked up as in Example 1 to afford white powder of conduritol A.

Test Example 1: Sugar Absorption Test in Reversed Gut 8 weeks old Wistar rats were anesthetized intraperitoneally with 1 ml/Kg body weight of Nembutal ® (sodium pentobarbital). The rats were abdominally incised, jejunum was excised from rats and washed with Ringer's solution containing 5 mM glucose. The guts were reversed using glass rod and thus reversed guts of about 30 mm in length were prepared. One end of each of the reversed guts was sealed by fastening. Then, the inside of the gut was filled with 400 μl of Ringer's solution containing 5 mM glucose, and the other end was fastened. The outside of the gut was filled with 10 ml of Ringer's solution containing 0.05 mg/ml, 0.1 mg/ml or 0.2 mg/ml of conduritol A in addition to 5 mM glucose. After 30 minutes at 36° C., the difference in the concentration of glucose between the inner solution and the outer solution was determined using Blood Sugar Test Kit (Boehringer Mannheim Yamanouchi).

The results are shown in Table 1.

TABLE 1

| Concentration of Added Conduritol A (mg/ml) | Difference in Glucose Concentration (mM) |
|---|---|
| 0 | 2.65 |
| 0.05 | 2.25 |
| 0.1 | 0.90 |
| 0.2 | 0 |

As evident from Table 1, absorption of glucose by the gut can completely be inhibited in the presence of 0.2 mg/ml of conduritol A.

Test Example 2: Therapeutic Effect of Conduritol A

Ten SD male rats (weight about 230 g) of 8 weeks old were used in this test. Animals were divided into 2 groups of 5 rats each and fasted for 12 hours. Then, one group received 1 g/Kg body weight of glucose alone and the other group received 1 mg/Kg of conduritol A in addition to 1 g/Kg of glucose, using esophageal sonde. Blood was taken from the tail vene at 15, 30, 60, 90 and 120 minutes after administration and the blood glucose level was determined.

The determination of glucose concentration was performed as in Example 1. The results are shown in Table 2 wherein the data shown are mean values of 5 aminals. The initial glucose level was set as zero.

TABLE 2

| Time (min) | Glucose Concentration in Blood (mg/dl) | |
|---|---|---|
| | Glucose alone | Glucose + Conduritol A |
| 0 | 0 | 0 |
| 15 | 105 | 75 |
| 30 | 91 | 64 |
| 60 | 36 | 30 |
| 90 | 28 | 14 |
| 120 | 20 | 0 |

As evident from the data of Table 2, an increase in blood sugar level can effectively be inhibited by the administration of conduritol A.

Test Example 3: Acute Toxicity

Acute toxicity of conduritol A was determined using 5 aminals each of male and female rats. Rats were still normal after administration of 2000 mg/Kg body weight oral dose of conduritol A. Such dose is the maximal according to OECD (Organization for Economic Cooperation and Development) guideline. Therefore, $LD_{50}$ value of conduritol A in the case of oral administration to rat is considered more than 2000 mg/Kg. Conduritol A of the agent of the present invention is thus a medicament of high safety.

Example 3: Preparation of Tetraacetyl Conduritol A 1 g of conduritol A was dissolved in 20 ml of pyridine. To this mixture, 3.36 ml of acetic anhydride was added, and the whole was left standing at room temperature for 24 hours with stirring. Then, the mixture was poured into 300 ml of ice-cold distilled water, and pyridine was removed. The aqueous layer was extracted with 100 ml of ethyl ether, and the ether extract was washed twice with 30 ml of 0.1N HCl, dried over anhydrous sodium sulfate and the solvent was distilled off under reduced pressure. The product was monitored by thin layer chromatography, and purified by silicagel column chromatography (1 cm×30 cm, 15 ml packed) to give 500 mg of acetylated conduritol A (tetraacetyl conduritol A).

Example 4: Preparation of Dihydroconduritol A 1 g of conduritol A was dissolved in a small amount of ethanol in 200-ml eggplant type flask. The resultant solution was subjected to catalytic reduction using 0.5 g of palladium/active carbon under hydrogen atmosphere for about 5 hours with stirring. After hydrogenation, the palladium catalyst was filtered off using No. 2 filter paper, and the filtrate was distilled under reduced pressure to remove ethanol. The residue was dissolved in a small amount of hot ethanol, then cooled to −20° C. whereby crystals precipitated which were separated by filtration with No. 2 filter paper and dried in a desiccator to give 800 mg of hydrogenated conduritol A (dihydroconduritol A).

Example 5: Preparation of Conduritol A Epoxide 800 mg of conduritol A and 1,448 mg of m-chloroperbenzoic acid were dissolved in 120 ml of methanol and the resultant mixture was stirred at room temperature for 4 days. Then, methanol was evaporated and the remaining residue was washed thrice with 80 ml of ether to remove chlorine compounds. Ether was removed off and the residue was then dissolved in as small amount of ethanol as possible, and allowed to crystallize by cooling to −20° C. The crystals were filtered with No. 2 filter paper and dried in a dessicator over night to give 400 mg of conduritol A epoxide.

Test Example 4: Sugar Absorption Test in Reversed Gut 8 weeks old Wistar rats were anesthetized intraperitoneally with 1 ml/Kg body weight of Nembutal ® (sodium pentobarbital). The rats were abdominally incised, jejunum was excised from rats and washed with Ringer's solution containing 5 mM glucose. The guts were reversed using glass rod and thus reversed guts of about 30 mm in length were prepared. One end of each of the reversed guts was sealed by fastening. Then, the inside of the gut was filled with 400 μl of Ringer's solution containing 5 mM glucose, and the other end was fastened. The outside of the gut was filled with 10 ml of Ringer's solution containing 0.1 mg/ml, 0.2 mg/ml or 0.3 mg/ml of dihydroconduritol A in addition to 5 mM glucose. After 30 minutes at 36° C., the difference in the concentration of glucose between the inner solution and the outer solution was determined using Blood Sugar Test Kit (Boehringer Mannheim Yamanouchi).

The results are shown in Table 3.

TABLE 3

| Concentration of Added Dihydroconduritol A (mg/ml) | Difference in Glucose Concentration (mM) |
|---|---|
| 0 | 2.70 |
| 0.1 | 1.65 |
| 0.2 | 0.80 |
| 0.3 | 0 |

As clearly shown in Table 3, absorption of glucose by the gut can completely be inhibited in the presence of 0.3 mg/ml of dihydroconduritol A.

Test Example 5: Sugar Absorption Test in Reversed Gut

The procedure of Test Example 4 was repeated using 0.1 mg/ml, 0.2 mg/ml, 0.3 mg/ml or 0.4 mg/ml of conduritol A epoxide.

The results are shown in Table 4.

TABLE 4

| Concentration of Added Conduritol A Epoxide (mg/ml) | Difference in Glucose Concentration (mM) |
|---|---|
| 0 | 2.70 |
| 0.1 | 1.80 |
| 0.2 | 1.55 |
| 0.3 | 0.85 |
| 0.4 | 0 |

As evident from Table 4, absorption of glucose by the gut can completely be inhibited in the presence of 0.4 mg/ml of conduritol A epoxide.

Test Example 6: Therapeutic Effect of Conduritol A Derivatives

The same procedure as in Test Example 2 was followed using 5 groups of animals each consisting of 5 SD male rats (weight about 230 g) of 8 weeks old. One group received 1 g/Kg body weight of glucose alone. The other 4 groups received 10 mg/Kg of conduritol A, 10 mg/Kg of tetraacetyl conduritol A, 10 mg/Kg of dihydroconduritol A or 10 mg/Kg of conduritol A epoxide, respectively, in addition to 1 g/Kg of glucose, using esophageal sonde. Blood was taken from the tail vene at 15, 30, 60 and 120 minutes after administration and the blood glucose level was determined.

The determination of glucose concentration was performed as in Test Example 1. The results are shown in Table 5.

TABLE 5

| | Glucose Concentration in Blood (mg/dl) | | | | |
|---|---|---|---|---|---|
| Time (min) | Glucose | Glu + Conduritol A | Glu + Ac-Conduritol A | Glu + Dihydroconduritol A | Glu + Epoxide |
| 0 | 0 | 0 | 0 | 0 | 0 |
| 15 | 80 | 52 | 49 | 42 | 59 |
| 30 | 73 | 60 | 65 | 50 | 67 |
| 60 | 43 | 36 | 40 | 44 | 45 |
| 120 | 20 | 13 | 12 | 11 | 16 |

As evident from the data of Table 5, an increase in blood sugar level can effectively be inhibited by the administration of tetraacetyl conduritol A, dihydroconduritol A, or conduritol A epoxide in comparable degree to or even more than that of conduritol A.

Test Example 7: Acute Toxicity of Conduritol A Derivatives

Acute toxicity of tetraacetyl conduritol A, dihydroconduritol A, and conduritol A epoxide was determined in an analogous way as in Test Example 3. Rats were still normal after administering 2000 mg/Kg body weight each of oral dose. Such dose is the maximal according to OECD (Organization for Economic Cooperation and Development) guideline. Therefore, $LD_{50}$ value of these conduritol A derivatives are considered more than 2000 mg/Kg. The active components of the present invention are thus extremely safe.

What is claimed is:

1. A method of inhibiting an increase in blood sugar level comprising employing an effective amount of a composition having as an active component conduritol A of the formula (I):

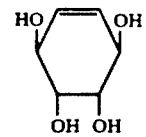

(I)

* * * * *